(12) United States Patent
So

(10) Patent No.: US 9,738,927 B2
(45) Date of Patent: Aug. 22, 2017

(54) METHOD AND APPARATUS FOR THE ANALYSIS AND IDENTIFICATION OF MOLECULES

(71) Applicant: Daniel Wai-Cheong So, Palo Alto, CA (US)

(72) Inventor: Daniel Wai-Cheong So, Palo Alto, CA (US)

(73) Assignee: Daniel Wai-Cheong So, Palo Alto, CA (US)

( * ) Notice: Subject to any disclaimer, the term of this patent is extended or adjusted under 35 U.S.C. 154(b) by 0 days.

(21) Appl. No.: 14/504,298

(22) Filed: Oct. 1, 2014

(65) Prior Publication Data

US 2015/0021183 A1 Jan. 22, 2015

Related U.S. Application Data

(63) Continuation of application No. 12/777,151, filed on May 10, 2010, now Pat. No. 8,926,904.

(Continued)

(51) Int. Cl.
*C12Q 1/68* (2006.01)
*G01N 33/487* (2006.01)
(Continued)

(52) U.S. Cl.
CPC ............ *C12Q 1/6869* (2013.01); *B32B 37/18* (2013.01); *B32B 38/10* (2013.01); *B82Y 30/00* (2013.01); *G01N 33/48721* (2013.01); *B01J 2219/00317* (2013.01); *B01J 2219/00427* (2013.01); *B01J 2219/00441* (2013.01); *B01J 2219/00509* (2013.01); *B01J 2219/00608* (2013.01); *B01J 2219/00653* (2013.01); *B01J 2219/00702* (2013.01); *B01J 2219/00722* (2013.01);

(Continued)

(58) Field of Classification Search
CPC ............ C12Q 1/6869; G01N 33/48721; Y10S 977/962; B01J 2219/00608; B01J 2219/00653; B01J 2219/00722; B01L 3/5027
See application file for complete search history.

(56) References Cited

U.S. PATENT DOCUMENTS 5,795,782 A 8/1998 Church et al.
6,015,714 A 1/2000 Baldarelli et al.
(Continued)

FOREIGN PATENT DOCUMENTS

CN 1606137 A 4/2005
CN 10225436 A1 7/2008
(Continued)

OTHER PUBLICATIONS

International Search Report mailed Jul. 9, 2010 for PCT Application No. PCT/US10/34602, filed May 12, 2010, 4 pages.
(Continued)

*Primary Examiner* — Paul Hyun
(74) *Attorney, Agent, or Firm* — Law Offices of Albert Wai-Kit Chan, PLLC

(57) ABSTRACT

An apparatus and method for performing analysis and identification of molecules have been presented. In one embodiment, a portable molecule analyzer includes a sample input/output connection to receive a sample, a nanopore-based sequencing chip to perform analysis on the sample substantially in real-time, and an output interface to output result of the analysis.

14 Claims, 20 Drawing Sheets

Related U.S. Application Data

(60) Provisional application No. 61/177,553, filed on May 12, 2009.

(51) Int. Cl.
  *B82Y 30/00* (2011.01)
  *B32B 37/18* (2006.01)
  *B32B 38/10* (2006.01)
  *B01L 3/00* (2006.01)

(52) U.S. Cl.
  CPC ....... *B01L 3/5027* (2013.01); *B32B 2305/026* (2013.01); *B32B 2307/202* (2013.01); *B32B 2310/0881* (2013.01); *B32B 2457/00* (2013.01); *Y10S 977/814* (2013.01); *Y10S 977/962* (2013.01)

(56) References Cited

U.S. PATENT DOCUMENTS

| | | |
|---|---|---|
| 6,267,872 B1 | 7/2001 | Akeson et al. |
| 6,362,002 B1 | 3/2002 | Denison et al. |
| 6,413,792 B1 | 7/2002 | Sauer et al. |
| 6,464,842 B1 | 10/2002 | Golovchenko et al. |
| 6,465,193 B2 | 10/2002 | Akeson et al. |
| 6,482,639 B2 | 11/2002 | Snow et al. |
| 6,616,895 B2 | 9/2003 | Dugas et al. |
| 6,627,067 B1 | 9/2003 | Branton et al. |
| 6,673,615 B2 | 1/2004 | Denison et al. |
| 6,746,594 B2 | 6/2004 | Akeson et al. |
| 6,783,643 B2 | 8/2004 | Golovchenko et al. |
| 6,806,534 B2 | 10/2004 | Dokumaci et al. |
| 6,806,543 B2 | 10/2004 | Yamakawa et al. |
| 6,846,702 B1 | 1/2005 | Barth |
| 6,905,878 B2 | 6/2005 | Ghadiri et al. |
| 6,936,433 B2 | 8/2005 | Akeson et al. |
| 7,001,792 B2 | 2/2006 | Sauer et al. |
| 7,060,507 B2 | 6/2006 | Akeson et al. |
| 7,189,503 B2 | 3/2007 | Akeson et al. |
| 7,238,485 B2 | 7/2007 | Akeson et al. |
| 7,258,838 B2 | 8/2007 | Li et al. |
| 7,347,921 B2 | 3/2008 | Barth et al. |
| 7,361,313 B2 | 4/2008 | Chan et al. |
| 7,410,564 B2 | 8/2008 | Flory |
| 7,435,353 B2 | 10/2008 | Golovchenko et al. |
| 7,468,271 B2 | 12/2008 | Golovchenko et al. |
| 7,504,505 B2 | 3/2009 | Shenoy et al. |
| 7,582,490 B2 | 9/2009 | Golovchenko et al. |
| 7,625,706 B2 | 12/2009 | Akeson et al. |
| 7,678,562 B2 | 3/2010 | Ling |
| 7,741,130 B2 | 6/2010 | Lee et al. |
| 7,883,839 B2 | 2/2011 | Donnelly et al. |
| 2003/0040173 A1 | 2/2003 | Fonash et al. |
| 2003/0136679 A1 | 7/2003 | Bohn et al. |
| 2004/0051154 A1 | 3/2004 | Yamakawa et al. |
| 2004/0144658 A1 | 7/2004 | Flory |
| 2005/0014162 A1 | 1/2005 | Barth et al. |
| 2005/0127035 A1 | 6/2005 | Ling |
| 2005/0202444 A1 | 9/2005 | Zhu |
| 2006/0063171 A1 | 3/2006 | Akeson et al. |
| 2006/0063196 A1 | 3/2006 | Akeson et al. |
| 2006/0231419 A1 | 10/2006 | Barth et al. |
| 2006/0275911 A1 | 12/2006 | Wang et al. |
| 2007/0048745 A1 | 3/2007 | Joyce et al. |
| 2007/0065832 A1 | 3/2007 | Stenger et al. |
| 2007/0131646 A1 | 6/2007 | Donnelly et al. |
| 2007/0178507 A1 | 8/2007 | Wu et al. |
| 2007/0281329 A1 | 12/2007 | Akeson et al. |
| 2007/0298511 A1 | 12/2007 | Kang et al. |
| 2008/0032290 A1 | 2/2008 | Young |
| 2008/0102504 A1 | 5/2008 | Akeson et al. |
| 2008/0187915 A1 | 8/2008 | Polonsky et al. |
| 2008/0248561 A1 | 10/2008 | Golovchenko et al. |
| 2008/0257859 A1 | 10/2008 | Golovchenko et al. |
| 2008/0280776 A1 | 11/2008 | Bashir et al. |
| 2009/0029477 A1 | 1/2009 | Meller et al. |
| 2009/0084688 A1 | 4/2009 | Leburton et al. |
| 2009/0130386 A1 | 5/2009 | Golovchenko et al. |
| 2009/0136682 A1 | 5/2009 | Branton et al. |
| 2009/0136958 A1 | 5/2009 | Gershow et al. |
| 2009/0298072 A1 | 12/2009 | Ju |
| 2010/0025249 A1 | 2/2010 | Polonsky et al. |

FOREIGN PATENT DOCUMENTS

| | | |
|---|---|---|
| WO | WO 2005/017025 A1 | 2/2005 |
| WO | 2008042018 | 8/2008 |

OTHER PUBLICATIONS

Written Opinion of the International Searching Authority mailed Jul. 9, 2010 for PCT Application No. PCT/US10/34602, filed May 12, 2010, 5 pages.

Loughran, Michael, "IBM Research Aims to Build Nanoscale DNA Sequencer to Help Drive Down Cost of Personalized Genetic Analysis", accessed at: http://www-03.ibm.com/press/us/en/pressrelease/28558.wss on Feb. 11, 2010, published Oct. 6, 2009, 3 pages.

Chiou, Chi-Han, et al., "Minimal dead-volume connectors for microfluidics using PDMS casting techniques", Journal of Micromechanics and Microengineering, vol. 14, Aug. 9, 2004, pp. 1484-1490.

Zhang, Chunsun, et al., "Micropumps, microvalves, and micromixers within PCR microfluidic chips: Advances and trends", Biotechnology Advances, vol. 25, 2007, pp. 483-514.

Gracheva, Maria E., et al., "Simulation of the electric response of DNA translocation through a semiconductor nanopore-capacitor", Nanotechnology, vol. 17, Jan. 6, 2006, pp. 622-633.

Branton, D. et al., "The Potential and Challenges of Nanopore Sequencing," Nature Biotechnology, Oct. 2008, pp. 1146-1153, vol. 26, No. 10.

Chinese First Office Action, Chinese Application No. 201080021139.4, Dec. 24, 2012, 12 pages.

Chinese Second Office Action, Chinese Application No. 201080021139.4, Oct. 30, 2013, 15 pages.

Clark, J. et al., "Continuous Base Identification for Single-Molecule Nanopore DNA Sequencing," Nature Nanotechnology, 2009, pp. 1-6.

Clarke, J. et al., Supplementary Information, Nature Nanotechnology, 2009, 17 pages.

De Blois, R.W. et al., "Electrokinetic Measurements with Submicron Particles and Pores by the Resistive Pulse Technique," Journal of Colloid and Interface Science, The Academic Press, Inc., Sep. 1977, pp. 325-335, vol. 61, No. 2.

De Blois, R.W. et. al., "Counting and Sizing of Submicron particles by the Resistive Pulse Technique," The Review of Scientific Instruments, Jul. 1970, pp. 909-916, vol. 41, No. 7.

Eid, J. et al., "Real-Time DNA Sequencing from Single Polymerase Molecules," Science, Jan. 2, 2009, pp. 133-138, vol. 323.

Kasianowicz, J.J. et al., "Characterization of Individual Polynucleotide Molecules Using a Membrane Channel," Proceedings of the National Academy of Sciences of the United States of America, Nov. 26, 1996, pp. 13770-13773, vol. 93, No. 24.

Xu, L. et al., "Nanopantography: A New Method for Massively Parallel Nanopatterning Over Large Areas," Nano Letters, 2005, pp. 2563-2568, vol. 5, No. 12.

Japanese Office Action, Japanese Application No. 2012-510988, Sep. 3, 2014, 6 pages.

Chinese Third Office Action, Chinese Application No. 201080021139.1, Sep. 15, 2015, 19 pages.

Chinese Fourth Office Action, Chinese Application No. 201080021139.4, May 14, 2015, 10 pages.

European Partial Search Report, European Application No. 15184138.4, Jun. 9, 2016, 7 pages.

Storm, A.J. et al., "Fabrication of Solid-State Nanopores with Single-Nanometre Precision," Nature Materials, Nature Publishing Group, Jul. 13, 2003, pp. 537-540, vol. 2, No. 8.

Oct. 17, 2016 Office Action, JP2015-196592.

(56) References Cited

OTHER PUBLICATIONS

Oct. 5, 2016 European Search Report, EP15184138.4.
Cui et al., Nanogap Electrodes towards Solid State Single-Molecule Transistors, Small, 2015, 11, No. 46, p. 6115-6141.
Ventra et al., Decoding DNA, RNA and peptides with quantum tunnelling, Nature Nanotechnology, vol. 11, Feb. 2016, p. 117-126.
Li et al., Nanogap Electrodes, Advanced Materials, 2010, 22, p. 286-300.

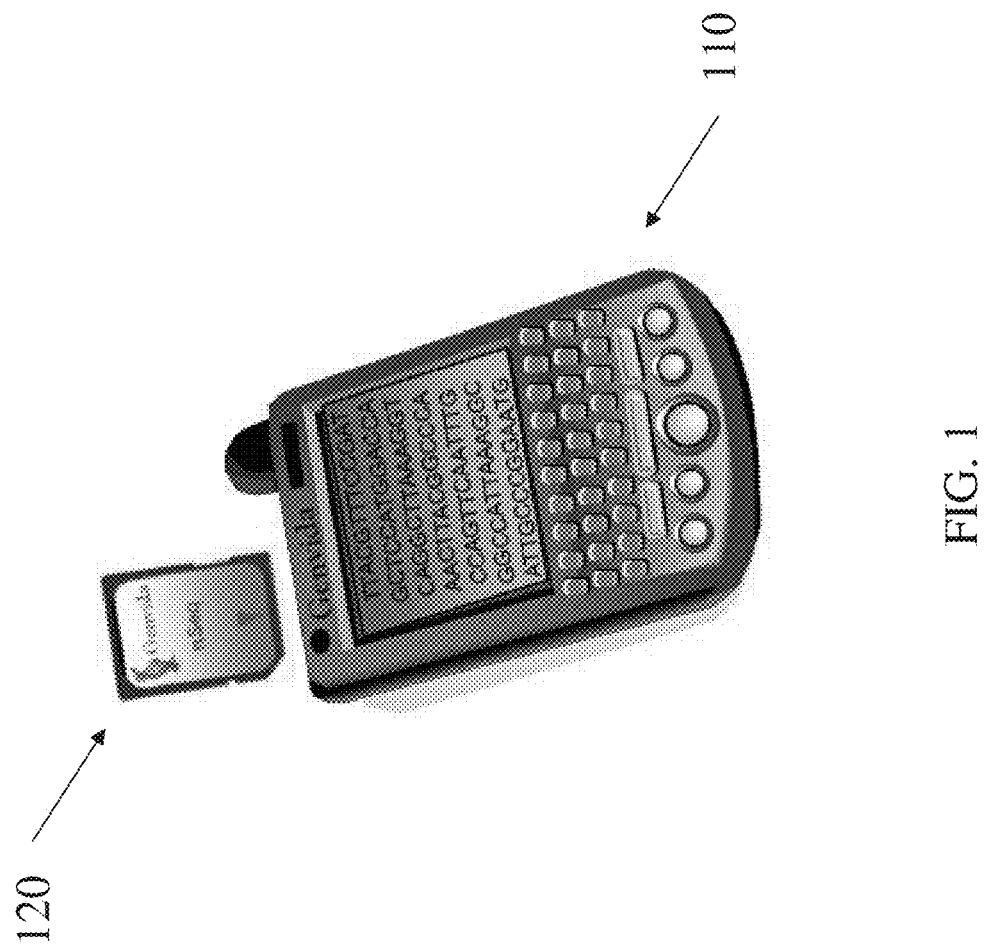

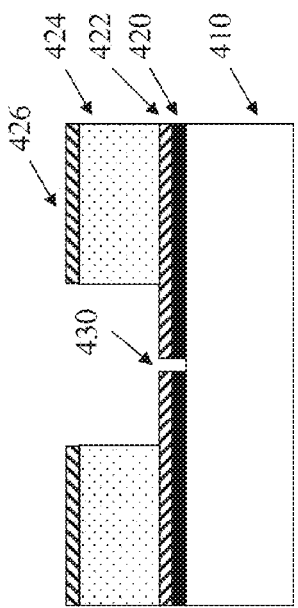
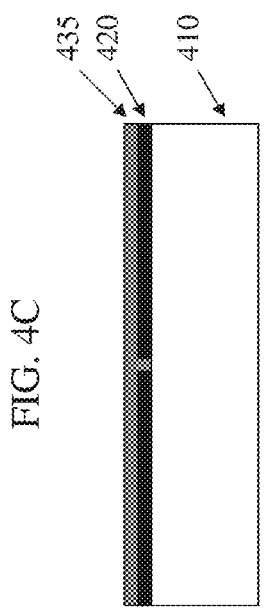
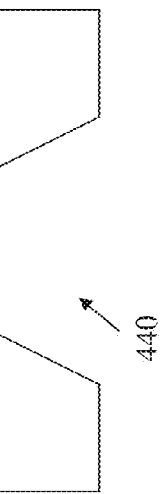
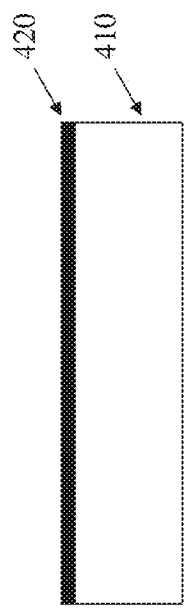
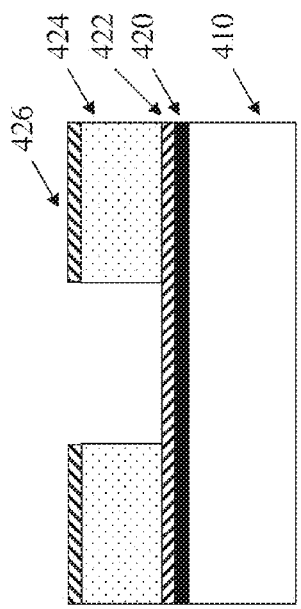

METHOD AND APPARATUS FOR THE ANALYSIS AND IDENTIFICATION OF MOLECULES

RELATED APPLICATIONS

This application is a continuation of U.S. patent application Ser. No. 12/777,151, filed May 10, 2010, which claims the benefit of U.S. Provisional Patent Application No. 61/177,553, filed May 12, 2009, which are herein incorporated by reference in their entirety.

TECHNICAL FIELD

The present invention relates generally to analyze and identify of molecules, and in particular to providing a real-time, portable, nanopore-based molecule analysis apparatus.

BACKGROUND

Nucleic acids, deoxyribonucleic acid (DNA), and/or ribose nucleic acid (RNA) are present and have unique sequences in every living organism. It lends itself naturally as a definitive identification for various bio-agents. Therefore, analysis of nucleic acids, DNA, and/or RNA, which is broadly referred to as genomic analysis herein, is very useful in studying living organisms. However, the currently commercially available nucleic acid sequencing technologies, such as microarray, pyrosequencing, sequencing by synthesis and sequencing by ligation are very limited in various aspects. For instance, some or all of these technologies cannot perform real-time analysis, require lengthy sample nucleic acid amplification procedures and protocols (such as polymerase chain reaction), have long turnaround time (typically takes about several days to weeks to analyze a small fragment of the sample nucleic acid), have high operation cost (some of which use expensive chemical reagents), have high false-positive error rates, and are non-portable.

Because of the above limitations of the current nucleic acid sequencing technologies, people working in the fields, such as medical professionals, security personnel, scientists, etc., cannot perform genomic analysis on-site locally. Rather, field workers have to collect and transport samples to specialized laboratories to be analyzed for days, or even weeks, in order to identify the nucleic acids present in the sample. Such lengthy tedious process can hardly meet today's need for genomic analysis, especially during epidemic outbreaks, such as the foot-and-mouth epidemic in United Kingdom, the Severe Acute Respiratory Syndrome (SARS) outbreak in Asia, and the recent H1N1 flu (also commonly known as swine flu) outbreak in Mexico and the United States. Using the current nucleic acid sequencing technologies, it is difficult, if not impossible, for the authorities to formulate a swift and informed decision, which could have an enormous safety and economic impact on the society.

To address the shortfalls of the above nucleic acid sequencing technologies, scientists have developed various nanopore-based sequencing technologies. Recently, Professor Hagan Bayley of Oxford University and his co-workers demonstrated long read with 99.8% accuracy using the α-haemolysin in a bio-nanopore experiment. Based on the established detection speed, an array of 256×256 nanopores is generally sufficient to analyze the human genome in its entirety within about thirty minutes. This would be a watershed triumph if one can successfully realize the bio-nanopore array. However, one drawback for bio-nanopores is the relative short lifetime, typically several hours to days, of the proteins and enzymes used in forming the bio-nanopores.

Solid state nanopore is a more robust alternative to bio-nanopore since there is no bio-reagent involved in the construction of the solid state nanopores. However, conventional lithography technologies employed in semiconductor industry are not capable of defining the 2-nm feature size required by the solid-state nanopore-based sequencing technologies. Thus far, different fabrication techniques, for instance, electron/ion milling, have been used to sequentially carve the nanopores one at a time. But these techniques cannot be scaled to produce the 256×256 array with affordable cost and reasonable production time.

BRIEF DESCRIPTION OF THE DRAWINGS

The present invention is illustrated by way of example, and not of limitation, in the figures of the accompanying drawings in which:

FIG. 1 illustrates one embodiment of a nanopore-based sequencer and an associated nanopore-based sequencing biochip;

FIGS. 4A-4E illustrate one embodiment of an subtractive method for fabricating a nanopore and/or a nanopore array;

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention.

Figure 2B:
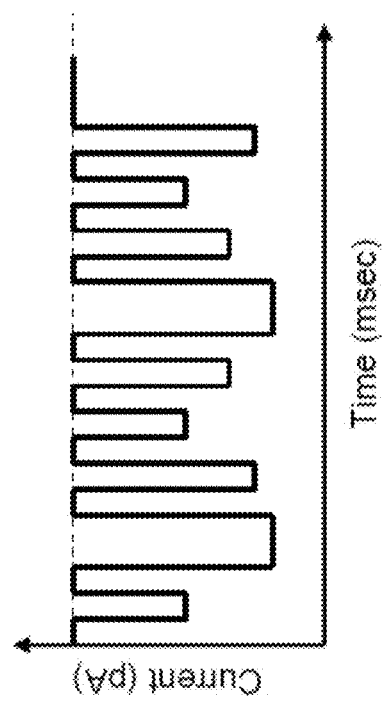
FIG. 2B illustrates a corresponding exemplary electrical readout of the nucleic acid sequence as compared with the background signal of an empty pore.
Figure 2A:
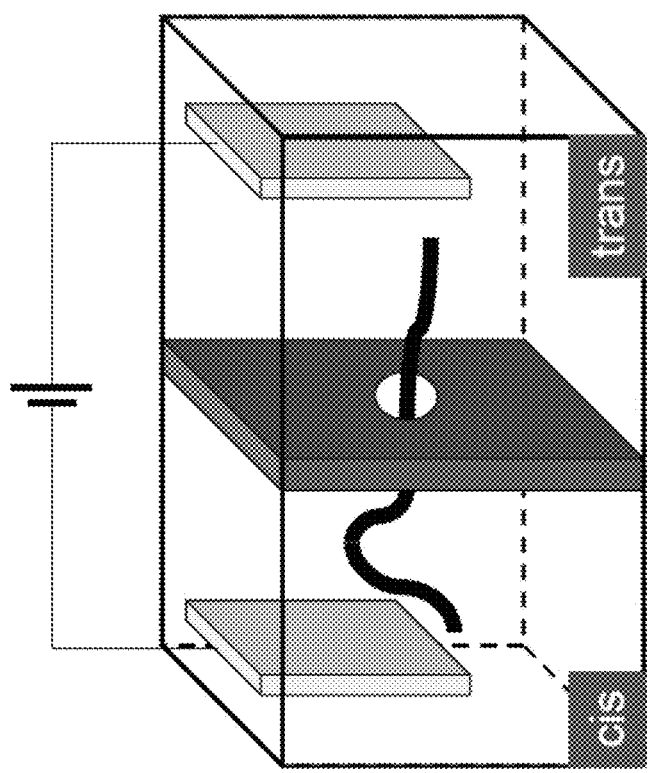
FIG. 2A illustrates one embodiment of a translocation process of a molecule during the detection and analysis of nanopore based nucleic acid sequencing.

Various embodiments of an apparatus and a method to perform analysis and identification of molecules, such as, nucleic acids, amino acids, peptides, proteins and polymers, and nanometer sized particles, such as carbon nanotubes, silicon nanorods and coated/uncoated gold nanoparticles, are described below. Note that the following discussion is focus on one example of molecule analysis, namely genomic analysis, in order to illustrate the concept. One of skilled in the art would readily recognize that the technique disclosed herein is applicable to analyze and identify molecules in general. In one embodiment, a nanopore-based sequencer is a portable genomic analysis system. FIG. 1 illustrates one embodiment of a portable nanopore-based sequencer 110 and an associated nanopore-based sequencing biochip 120. During detection and analysis, a molecule in a sample under test is electrophoretically driven in solution through a nanoscale pore (also referred to as a nanopore), as illustrated in FIG. 2A. In some embodiments, the size of the nanopore is about 2 nm. Note that the size of the nanopores may vary in different embodiments. For example, the nanopores are of fixed identical size in some embodiments. In some alternate embodiments, the nanopores are of different sizes. Furthermore, the shape of the nanopores may also vary in the same embodiment, or in different embodiments, such as circles, ovals, elongated slits, etc. Contingent upon the relative size and travelling speed of the molecule in the space confined within the nanopore, various electrical characteristics, such as current pulses of different amplitudes and durations, as represented in FIG. 2B, can be observed and utilized to identify the molecule. As a result, direct read of the nucleic acid sequence can be achieved without destroying the molecule under test. In other words, measurements can be made on the nucleic acid sequence while keeping the nucleic acid sequence intact.

Multiple fabrication techniques may be utilized to massively produce the nanopore array, which includes an array of about 2-nm pores in some embodiments, without fundamental limitations. Details of some exemplary fabrication techniques are discussed in details below to illustrate the concept. One of skill in the art would appreciate that other comparable fabrication techniques or variations to these techniques may be adopted to produce the nanopore array. By incorporating into a network of micro-/nano-fluidic channels, the nanopore-based sequencer can accurately decipher the genome with unprecedented speed and without human intervention.

Besides the small form-factor and speed in genomic analysis, some embodiments of the nanopore-based sequencer offer the following additional advantages. One of the advantages is ready production of future proof to any mutations in the bio-agents. This is possible because nanopore-based sequencing is a direct read technique whose results do not require prior knowledge of the genome under test. Furthermore, some embodiments of the nanopore-based sequencer are operable in extreme conditions and unclean environment because sterility and cleanliness are always ensured for the nanopores as the nanopores are always enclosed inside the nanopore-based sequencing biochip and are not exposed to any unwanted foreign substances during the entire analysis process.

As a handheld portable device, some embodiments of the nanopore-based sequencer can accelerate the advancement in many different industries and science. For instance, in commerce as well as research and development, some embodiments of the nanopore-based sequencer may be useful in basic research, pharmacogenomics, bacterial diagnostics, pathogen detection, agriculture, food industries, biofuel, etc. As further examples, some embodiments of the nanopore-based sequencer may be useful in rapid DNA forensics, port-of-entry bio-screening, etc.

Nanopore Array for Nanopore-Based Sequencing

In the 1970s, based on the resistive-pulse technique of the Coulter Counter, DeBlois and colleagues successfully demonstrated the use of single submicron diameter pores in characterizing particles by their sizes and electrophoretic mobility. Subsequently, Deamer proposed the idea of using nanometer sized pores for gene sequencing. He and his colleagues demonstrated that single-stranded DNA (ssDNA) and RNA molecules can be driven through a pore-forming protein and detected by their effect on the ionic current through this nanopore. Given the recently demonstrated high sequencing speed, the progress of nanopore-based sequencing is largely hampered by the lack of an inexpensive and parallel-write fabrication process to create a large array of nanopores for rapid genomic analysis. Many of the conventional lithography methods, electron milling, ion milling, and silicon etch back are not viable means to manufacture the nanopore array required for real-time genomic analysis. Until recently, Donnelly and colleagues in the University of Houston developed some embodiments of nanopantography that can massively produce 2-nm nanopore arrays without much limitations. According to their simulation results, nanopantography is capable of defining holes or dots with size as small as 1-nm. By incorporating the technologies of micro-/nano-fluidics, nanopantography opens up the possibility of achieving real-time or near real-time genomic analysis systems.

Figure 3:
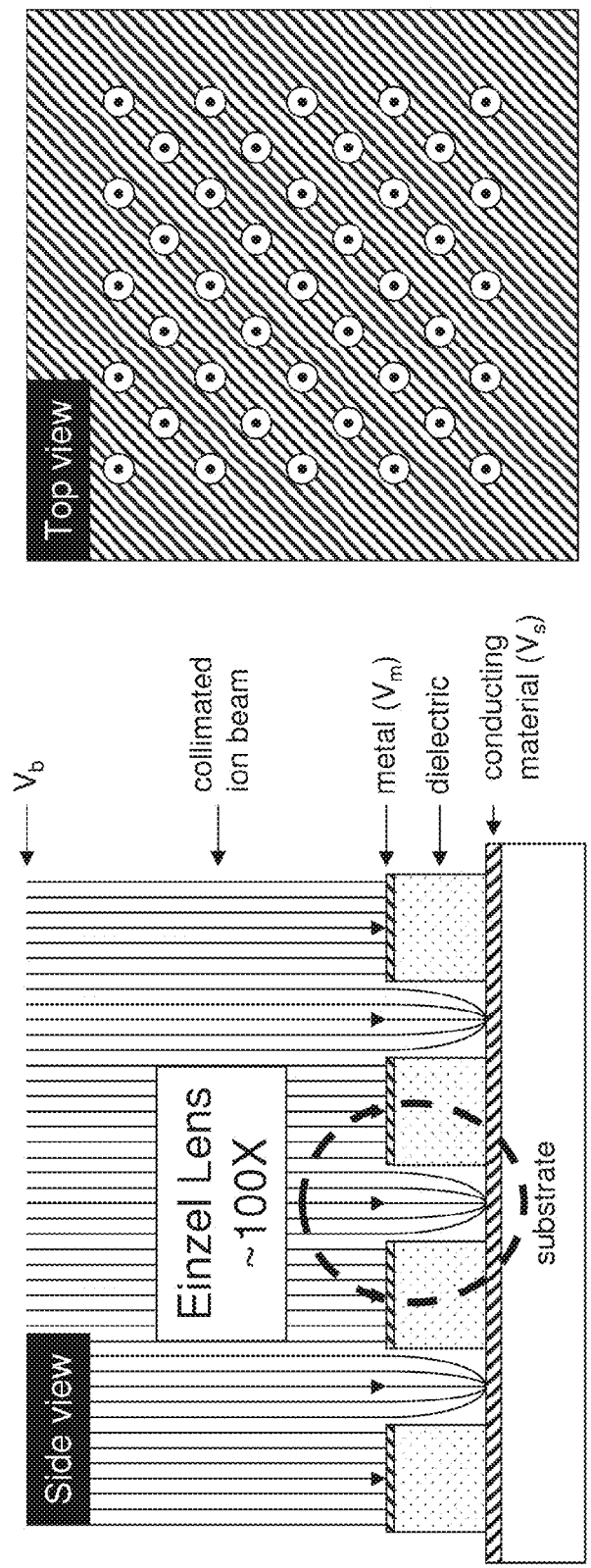
FIG. 3 illustrates a side view and a top view of one embodiment of an Einzel lens used in the nanopantography for both etch and deposition.

In nanopantography, a broad, collimated, monoenergetic ion beam is directed at an array of submicron-diameter electrostatic lenses (also referred to as Einzel lenses, as shown in FIG. 3) fabricated on the conductive substrate, e.g., doped silicon (Si) wafer. By applying appropriate voltages to the lens electrodes, the "beamlets" entering the lenses are focused to spots that can be 100 times smaller than the diameters of the lenses. This means a 1-nm feature can be defined by a 100-nm lens, which can be handled by the photolithographic techniques used in present semiconductor processing. Also, each lens writes its own nanometer feature on the substrate, therefore, nanopantography is a parallel-write process, very different from the sequential writing of the focused electron beam or ion beam. Because the lens array is part of the substrate, the method is substantially immune to misalignment caused by vibrations or thermal expansion. The size of the nanometer features is controlled by the size of the pre-defined lenses, whose diameters could be identical or different, i.e., an array of identical or different nanometer features can be processed substantially simultaneously. With an Ar+ beam in the presence of $Cl_2$ gas, 10-nm diameter, 100-nm deep etched Si holes have been demonstrated. Etching may occur only in the holes for which a voltage is applied to the top metal layer so that the ion beamlets are focused. The rest of the holes will have no voltage applied to the top metal layer, the beamlets will not be focused, and the current density will be too small to cause any appreciable etching.

With the nanopantography, there are two methods, namely the subtractive method and the additive method, to fabricate the nanopores for genomic analysis. One embodiment of a direct etch method is first discussed below, and then followed by discussion of one embodiment of an indirect etch method.

A. One Embodiment of a Subtractive Method for Fabricating Nanopores and/or Nanopore Array FIGS. 4A-4E illustrate one embodiment of a subtractive method for fabricating a nanopore and/or a nanopore array. Referring to FIG. 4A, nitride 420 is deposited on a Si (100) wafer 410. In FIG. 4B, the bottom conducting material 422, doped silicon or metal, is deposited, followed by the dielectric spacer 424, and the top metal layer 426. Then a number of Einzel lenses are defined. Referring to FIG. 4C, the nanopantographic etch is performed on the conducting material 422 to define the nanometer holes 430, which are used as hardmask for the nanopore etch in the nitride layer 420. In FIG. 4D, the Einzel lenses are removed. Then the nanopores 430 are coated with oxide 435 for protection. Finally, in FIG. 4E, the bottom cavity 440 of the measurement chamber is formed by chemical mechanical polishing (CMP), lithographic technique and potassium hydroxide (KOH) etch on the backside of the silicon substrate 410. The oxide layer 435 is then removed to reveal the nanopores 430.

Figure 5C:
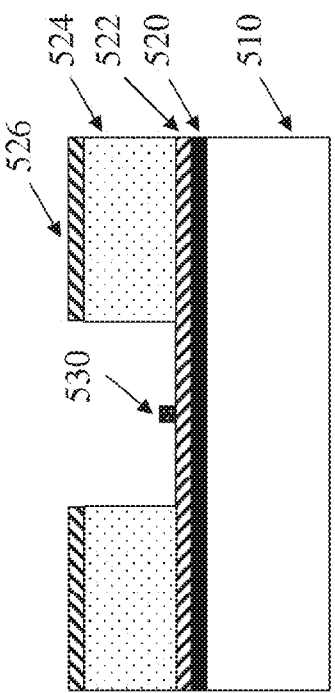
FIGS. 5A-5I illustrate one embodiment of a additive method for fabricating a nanopore and/or a nanopore array.
Figure 5D:
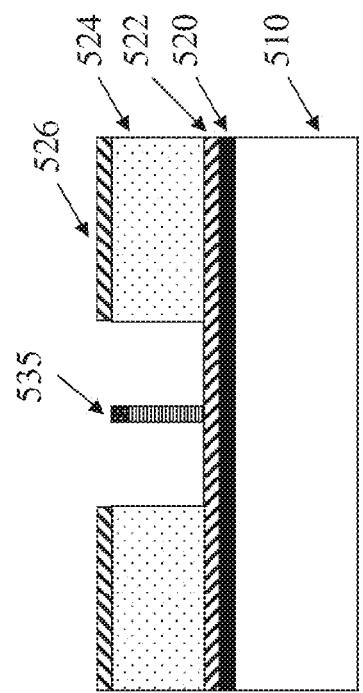
Figure 5A:
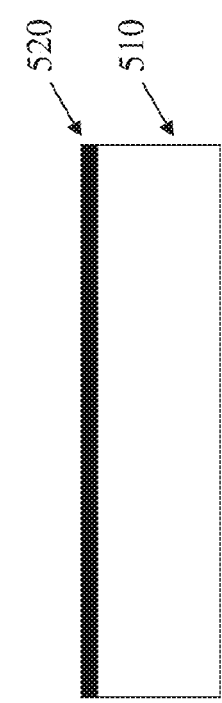
Figure 5B:
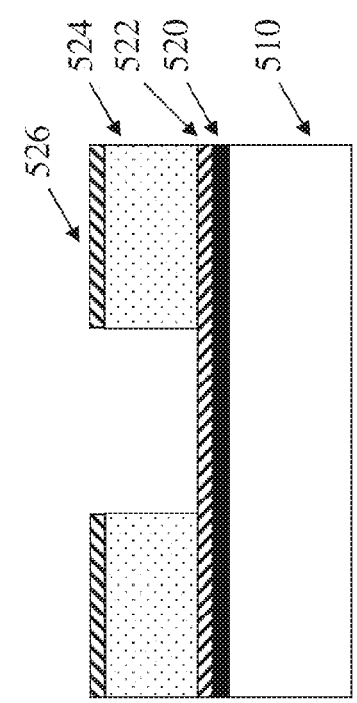
Figure 5G:
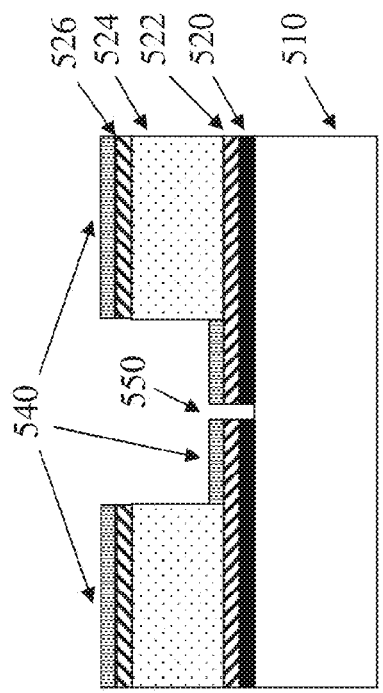
Figure 5E:
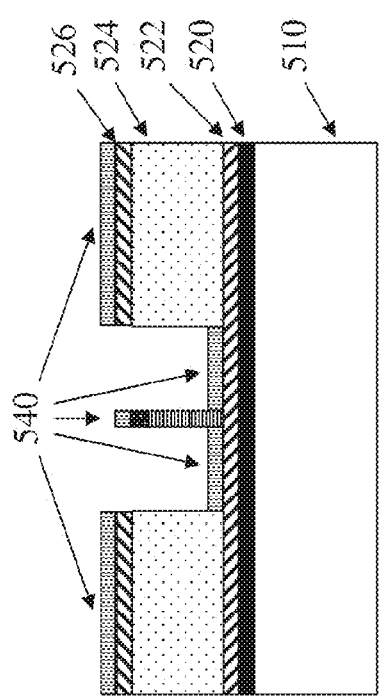
Figure 5F:
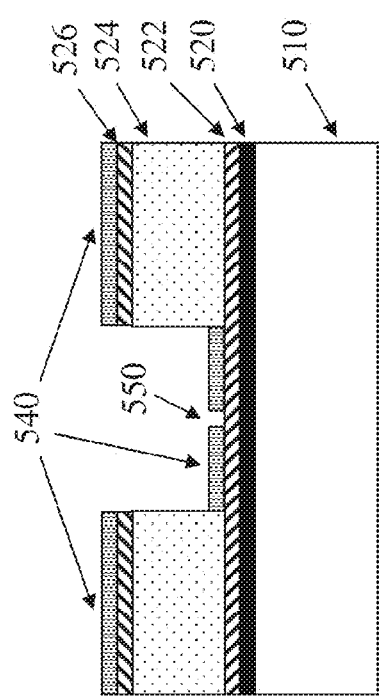
Figure 5H:
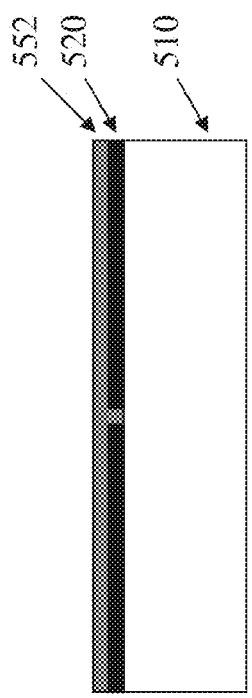
Figure 5I:
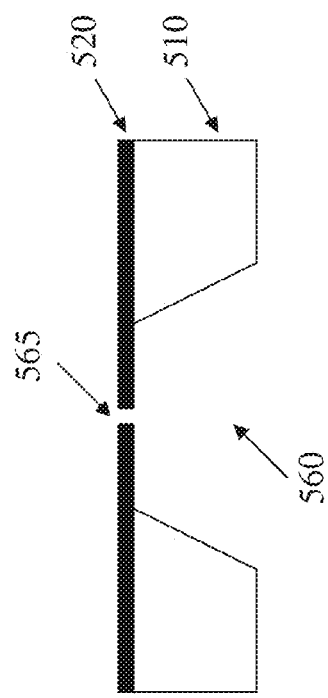

B. One Embodiment of a Additive Method for Fabricating Nanopore and/or Nanopore Array FIGS. 5A-5I illustrate one embodiment of an additive method for fabricating a nanopore and/or a nanopore array. Referring to FIG. 5A, nitride 520 is deposited on a Si (100) wafer 510. In FIG. 5B, the bottom conducting material 522, doped silicon or metal, the dielectric spacer 524, and the top metal layer 526 are deposited. Then the Einzel lenses are defined. In FIG. 5C, the nano-seed 530 for nanorod or nanotube growth is deposited. In FIG. 5D, the nanorod or nanotube 535 is grown. In FIG. 5E, oxide 540 is deposited. In FIG. 5F, the nanorod or nanotube 535 is removed. The remaining oxide nanometer hole 550 is used as hardmask for the conductive layer and the nitride layer. In FIG. 5G, a pattern is transferred from the oxide layer 540 to conductive layer 522, then to nitride layer 520. In FIG. 5H, the Einzel lenses are removed, followed by removal of the oxide layer 540. The nanopores are coated with oxide 552 for protection. Finally, in FIG. 5I, the bottom cavity 560 of the measurement chamber is formed by CMP, lithographic technique and KOH etch on the backside of the silicon substrate 510. The oxide layer 552 is then removed to reveal the nanopores 565.

Figure 6:
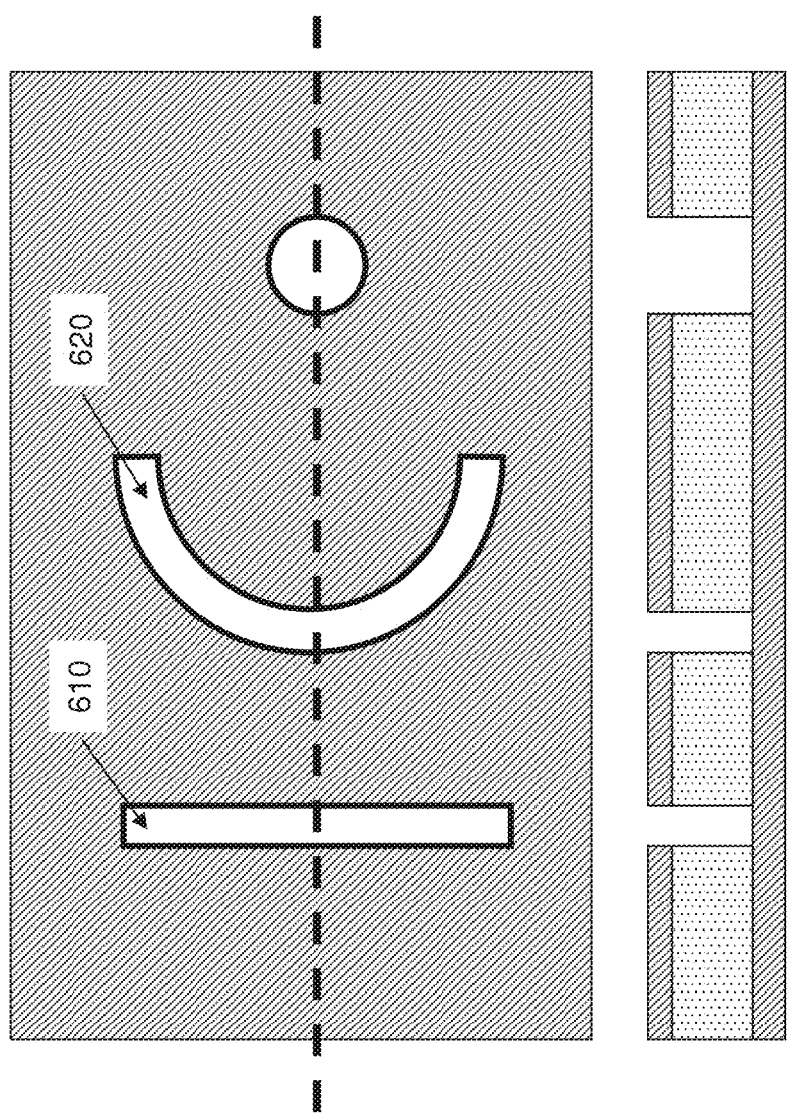
FIG. 6 illustrates one embodiment of a nanoring and one embodiment of a nanoslit.

FIG. 6 illustrates one embodiment of a nanoslit and one embodiment of a nanoring usable in some embodiments of the invention. The elongated nano-sized nanoslits 610 and nanorings 620 can be defined by some embodiments of the subtractive method with Einzel lenses (which is discussed above) with openings in the shape of a rectangle and a semi-circle, respectively, as depicted in FIG. 6. Based on the disclosure made herein, it should be apparent to one of skilled in the art that any two-dimensional shapes can be defined using similar patterning technique. Since the wafer stage is substantially stationary during the entire process in some embodiments, this non-circular patterning method solves at least three of the major technical issues confronted by the conventional method of tilting the wafer stage. First, there is no need for precise control of the tilting angle and speed of the wafer stage. Second, it generally overcomes the line-broadening effect and the line-width non-uniformity introduced by tilting the wafer relative to the incoming beam of ions. Third, it allows different shapes and sizes of patterns to be defined at about the same time.

Nanopore-Based Sequencing Biochip

Figure 7:
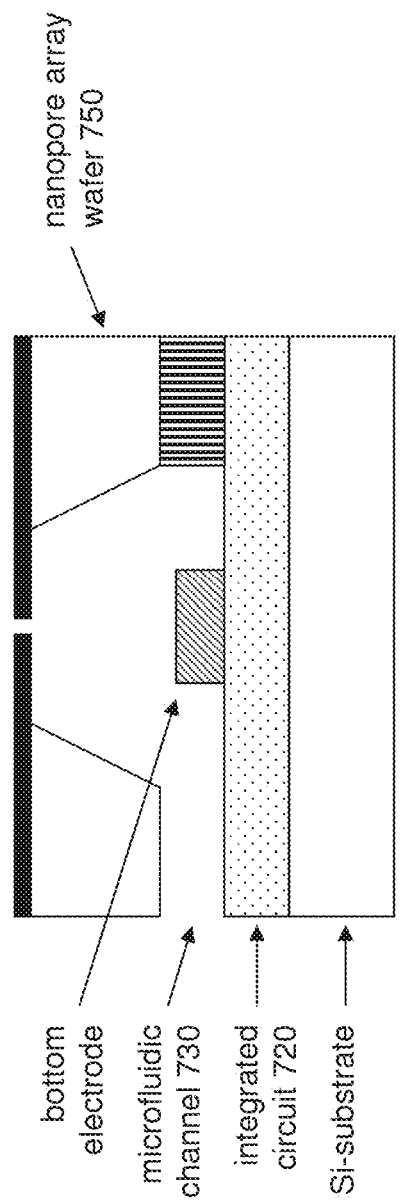
FIG. 7 illustrates one embodiment of a bonded nanopore array wafer and integrated circuit wafer to form the bottom cavity of a measurement chamber.

After the nanopore array is formed with either the subtractive or additive method, the nanopore array wafer 750 can be bonded onto a wafer with pre-fabricated integrated circuits 720 and microfluidics channels 730, as shown in FIG. 7. This completes the formation of the bottom cavity of the measurement chamber. The nucleic acid sample can be extracted out of the biochip through the microfluidic channels on the bottom wafer if desired.

Figure 8:
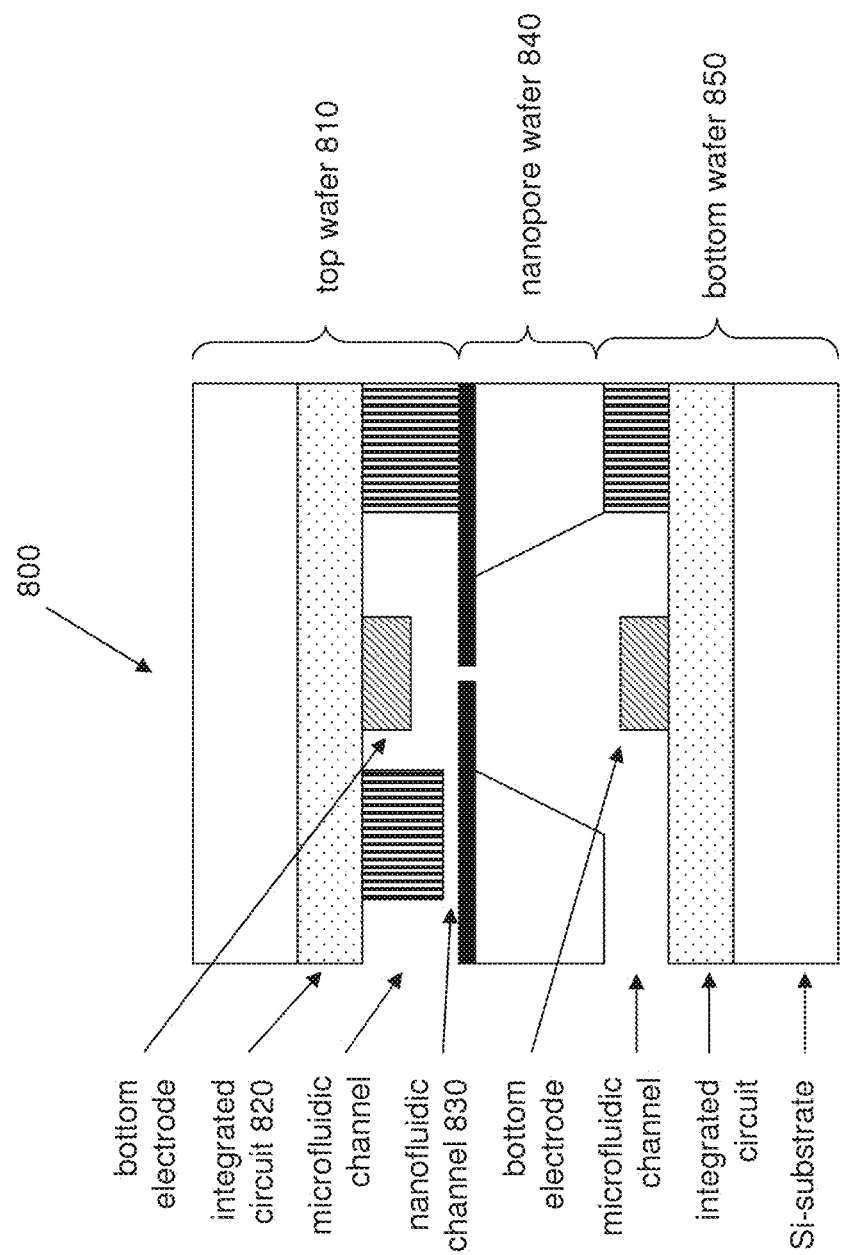
FIG. 8 illustrates one embodiment of a bonded top wafer and composite wafer to form the top cavity of the measurement chamber.
Figure 9:
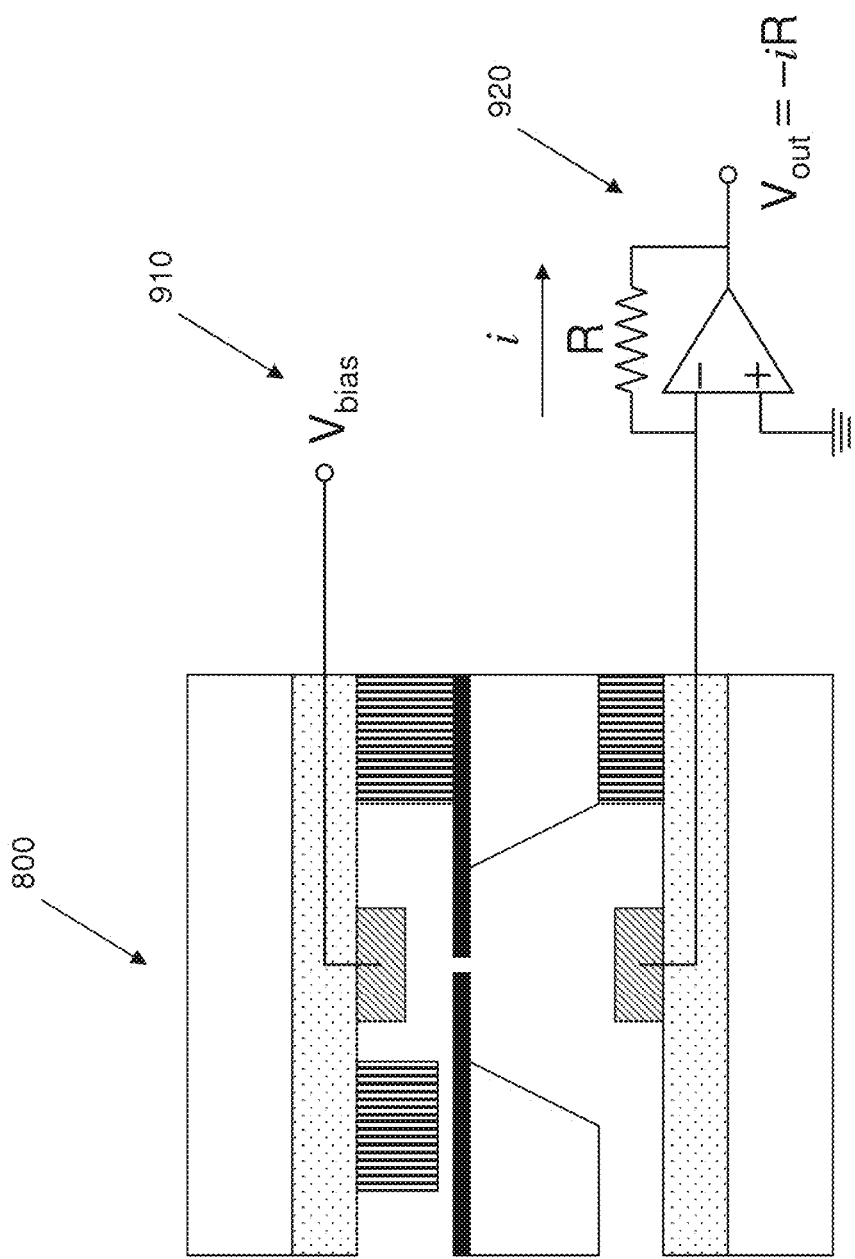
FIG. 9 illustrates one embodiment of a voltage biasing scheme and current sensing circuit operable with a nanopore-based sequencer.

Similarly, in some embodiments, the top cavity of the measurement chamber is formed by bonding a top wafer 810 with the integrated circuit 820 and/or the fluidic channels 830 onto the composite wafer, which includes the bonded nanopore wafer 840 and the bottom wafer 850. This trilayer wafer structure 800 is illustrated in FIG. 8. One embodiment of the voltage biasing scheme 910 and the associated current sensing circuit 920 are depicted in FIG. 9. With proper fluid I/O connections, such as those with minimal dead-volume, the trilayer composite wafer 800 is then mounted on a supporting frame for wire bonding or bell grid wire bonding. Typical packaging techniques, for example, epoxy encapsulation and ceramic packaging, can be used to enclose the whole assemble to form the nanopore-based sequencing biochip. Alternatively, integrated circuits, such as those associated with sensing and biasing, may be fabricated on the nanopore wafer 840, which may be bonded to blank substrate instead of another wafer having integrated circuits thereon.

Figure 10A:
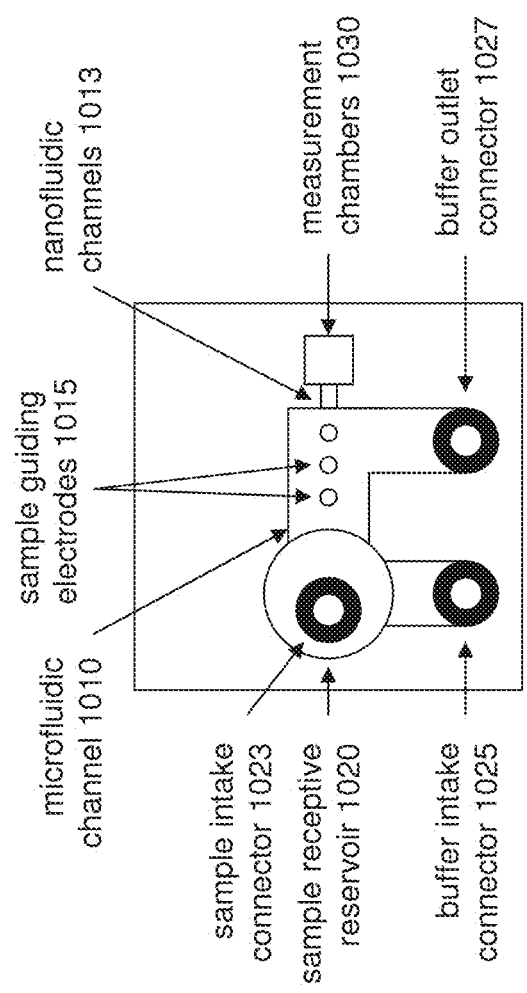
FIG. 10A illustrates one embodiment of a nanopore-based sequencer.
Figure 11:
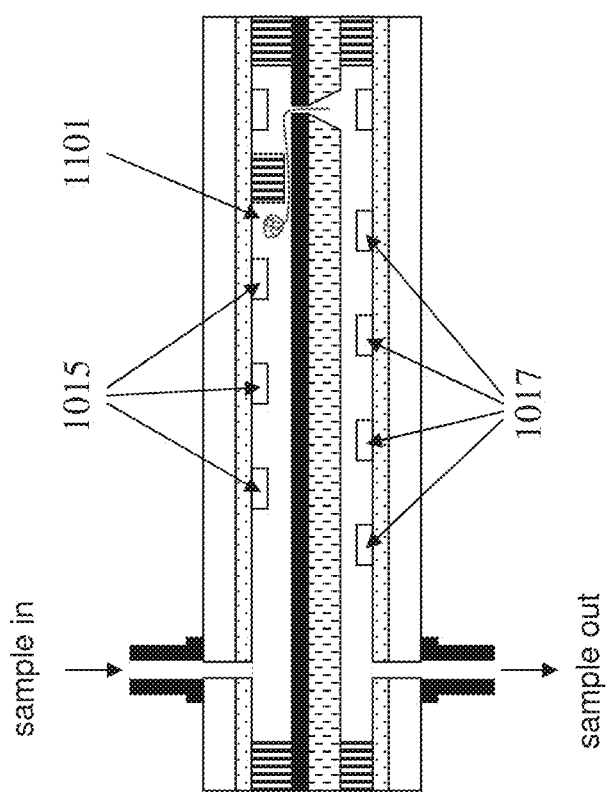
FIG. 11 illustrates a cross-sectional view of one embodiment of a nanopore-based sequencer along a selected path from the sample intake, along the microfluidic channel and the nanofluidic channel, through the measurement chamber, then to the sample outlet.

Furthermore, in some embodiments, there are two more features embedded on the top wafer 810, namely the sample guiding electrodes 1015 along the microfluidic channel 1010 and the nanofluidic channel 1013 leading to the measurement chamber 1030, as shown in FIGS. 10A and 11. To further illustrate the flow of sample through the nanopore-based sequencing biochip, one example is discussed in details below.

The buffer intake 1025 and buffer outlet 1027 are for pre-wet and pre-fill the network of microfluidic channel 1010, the nanofluidic channel 1013 and the measurement chamber 1030 before the intake of the sample for detection. During detection, the fluid flow in the microfluidic channel can be adjusted by the flow rate of the buffer intake and outlet using the on-chip or off-chip micropumps and microvalves.

In one example, the phosphate-deoxyribose backbone of a single strand nucleic acid molecule is charged with a negative charge for each base segment, and there are two negative charges at the 5'-end of the molecule. A positive voltage pulsating along the sample guiding electrode chain 1015 from the receptive reservoir 1020 through the sample intake connector 1023 to the destined measurement chamber 1030 can extract the nucleic acid molecule from the receptive reservoir 1020 and deliver the molecule to the pre-assigned measurement chamber 1030. Likewise, sample guiding electrodes 1017 also are embedded on the bottom wafer along the microfluidic channels 1010 for extracting the samples out of the nanopore-based sequencing biochip in a similar way.

Figure 10B:
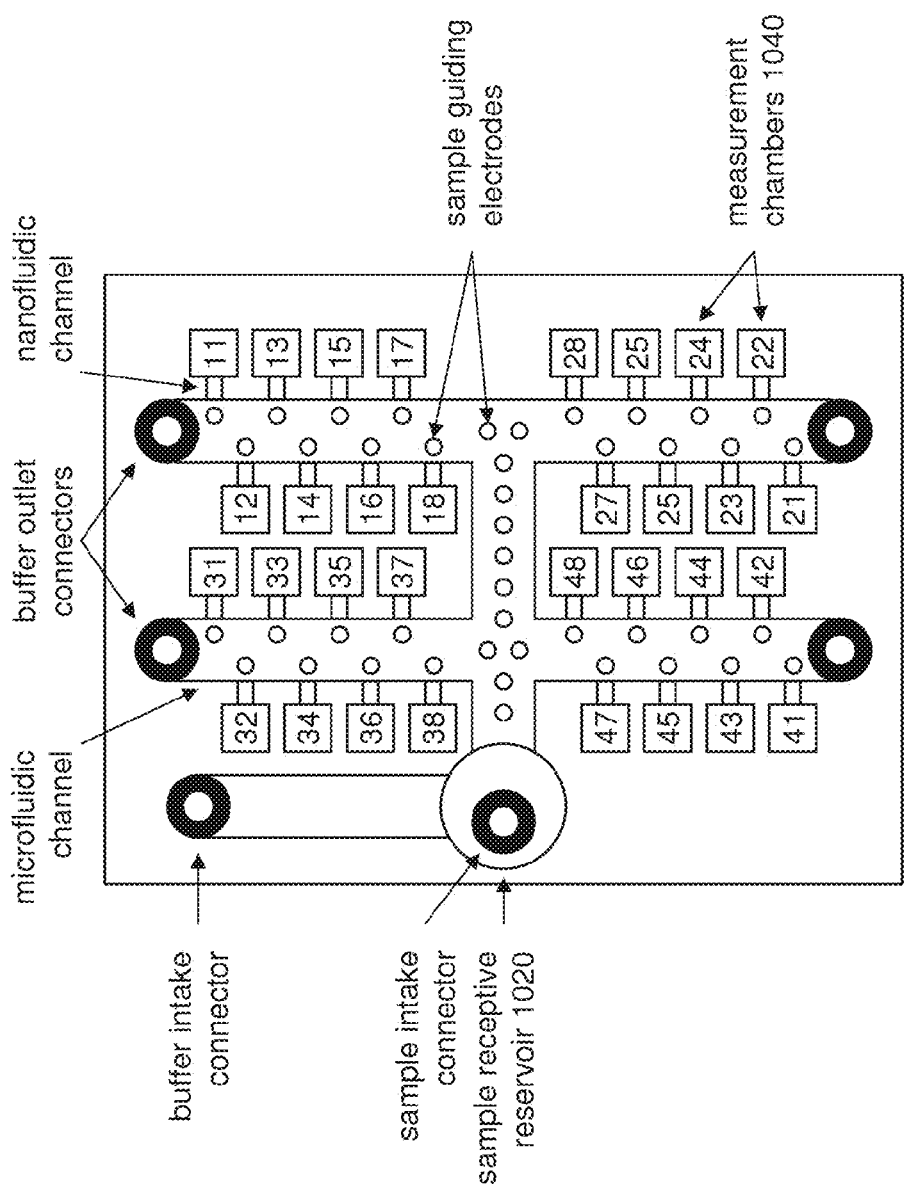
FIG. 10B illustrates one embodiment of multiple measurement chambers.

Using similar scheme of sample guiding electrodes along the network of fluidic channels, one can extend the number of measurement chambers 1040 to more than one. An example of the measurement chambers arranged in a tree architecture is illustrated in FIG. 10B. Besides the ability to perform multiple independent analyses, the order of the DNA fragments as they are being extracted from the sample receptive reservoir 1020 is pre-assigned to each measurement chamber in some embodiments. As shown in FIG. 10B, the measurement chambers 1040 are labeled with a 2-digit number. The first digit denotes the branch number and the second digit indicates the position of the measurement chamber in a branch. The assignment order of the measurement chambers 1040 may simply be in the ascending order, i.e., the chamber with the lowest number can be used first and then the chamber with next higher number. In this way, all of the measurement chambers in a branch can be used before moving onto the next branch. Alternatively, the samples can be assigned to the chambers with the lowest number in each branch with the lowest branch number being used first, i.e., 11, 21, 31, 41 then 12, 22, 32, 42, so on and so forth in the current example. According to this assignment approach, the measurement chamber of each branch with the furthest distance from the central microfluidic channel may be assigned first, then the next one of each branch. This approach may reduce the interference of the electrical signal of the sample guiding electrodes in the central microfluidic channel onto the measured signals. When the overall measurement is completed, the sequence of the entire DNA sample can be systematically assembled according to the order of extraction of the fragments. This may eliminate the time consuming post detection analysis required by other conventional sequencing technologies, such as, microarray, in which the hybridization process randomizes the original sequence of the sample and a computation intensive and error-prone post-detection analysis is required to piece back the proper sequence. Furthermore, since the order of extraction of the fragments is recorded, the fragments can be recombined to form the original DNA sample. For the other conventional sequencing technologies, the original sample is typically destroyed and cannot be retrieved for future use.

Referring back to FIG. 10A, the nanofluidic channel 1013 formed by wafer bonding of the top and composite wafer may serve as a filter, a sample flow rate controller, as well as a molecule stretcher. In some embodiments, the nanofluidic channel serves as a filter by turning on and off the top electrode on the top wafer, one can selectively pull in the sample from the microfluidic channel. In some embodiments, the nanofluidic channel serves as a sample flow rate controller by adjusting the voltages of the top and bottom electrodes, one can control the flow rate of the sample through the nanofluidic channel. The nanofluidic channel 1013 may also serve as a molecule stretcher because the single strand nucleic acid molecule 1101 may be stretched out from the natural curl up state when it passes through the nanofluidic channel 1013, as depicted in FIG. 11.

Figure 12:
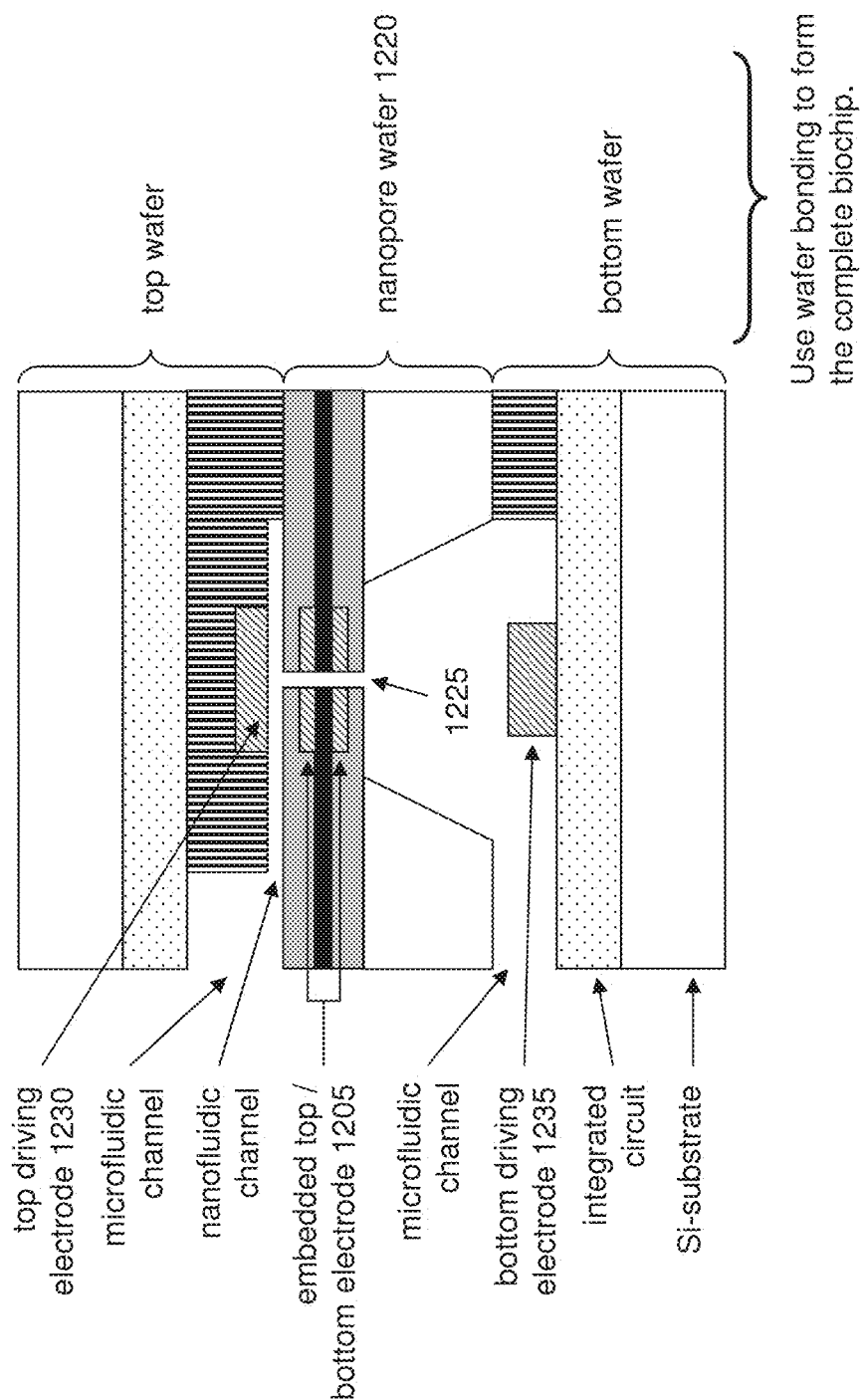
FIG. 12 illustrates one embodiment of a trilayer biochip structure with embedded electrodes.

In some embodiments, the speed control properties of the nanofluidic channels are exploited to allow more accurate analyses of molecules. As illustrated in FIG. 12, the sensing electrodes 1205 are embedded in the nanopore 1225, which become an integral part of the micro-/nano-channel network in controlling the flow of the molecules through the nanopore 1225. In addition to the nanofluidic channel, the applied DC voltages are designed to fine tune the speed and the direction of the molecules when translocating through the nanopore 1225. By alternating the magnitude of the DC biasing voltages applied to the top and bottom driving electrodes 1230 and 1235, respectively, and the embedded sensing electrodes 1205, the molecule under test can be drawn through the nanopore 1225 back and forth multiple times for repeated analyses, in order to increase the accuracy in identifying the molecules by eliminating the statistical error, i.e., the false-positive error rate can be reduced.

Unlike some conventional approach, where the sensing electrodes are integrated into the nanopore, it might only take several nanoseconds for each base in the DNA to travel through the nanopore. Such transit time is too short for any meaningful measurement. In view of this shortcoming, other conventional approaches have been developed to slow down the movement of molecules through the nanopore. One conventional approach proposes a voltage trapping scheme to control the speed of the molecules by embedding extra electrodes into the nanopore. The proposed voltage trapping scheme is difficult to implement since it requires four or more conducting electrodes stacked on top of each other and electrically insulated from each other by sandwiching dielectric material in between the conducting electrodes. The required 2-3 nm nanopore forms on this multi-layer film may have an aspect ratio of more than 30:1, which is difficult, if not impossible, to achieve with the current integrated circuit fabrication technologies.

Figure 13A:
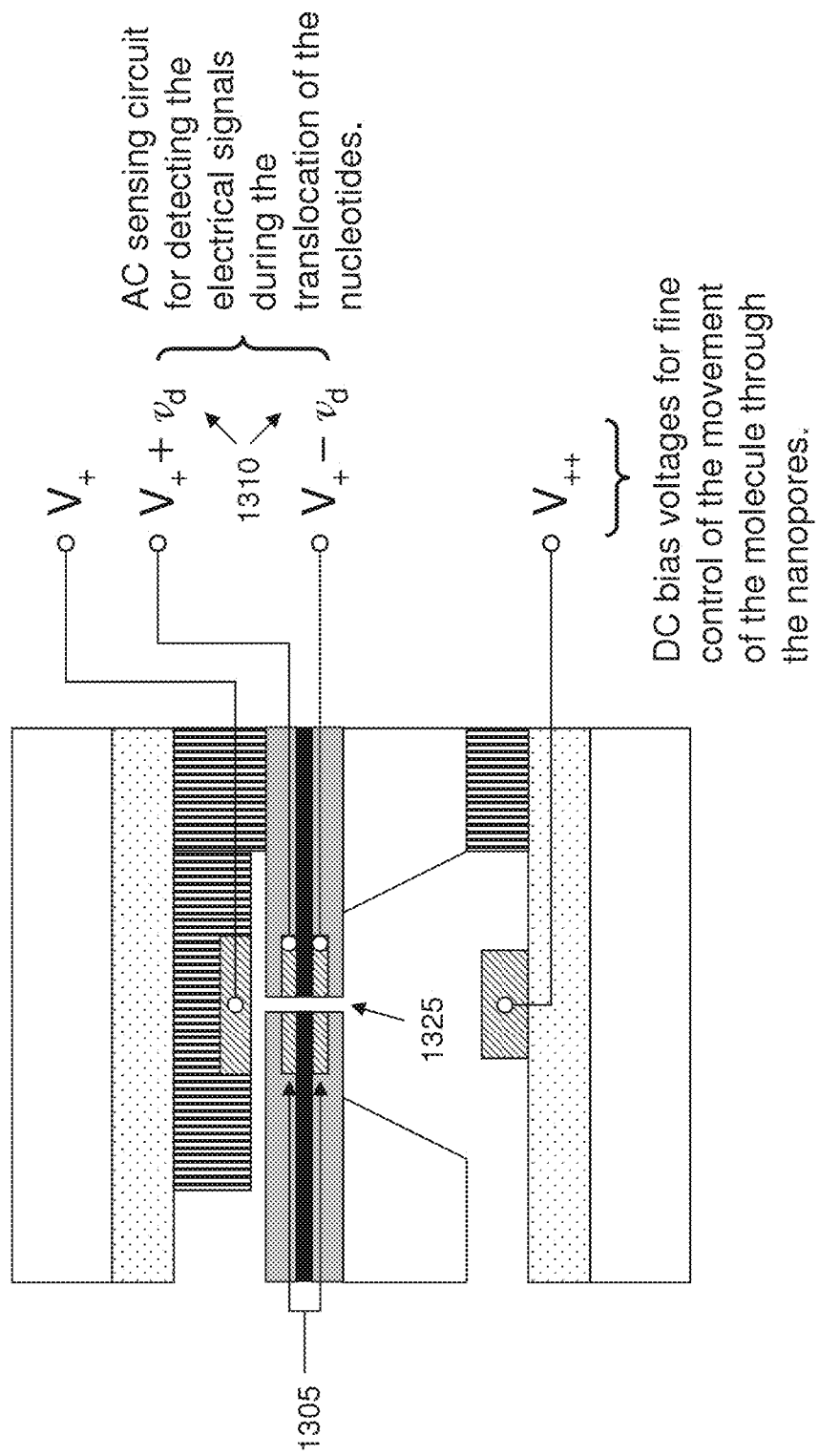
FIG. 13A illustrates one embodiment of a biasing and sensing scheme for nanopore detection.

As shown in FIG. 13A, the applied AC sensing voltages 1310 are for interrogating the molecules while they are translocating through the nanopore 1325. Consequently, various sensing mechanisms can be employed to identify the molecule, for instance, change in resistance, change in capacitance, change in phase and/or tunneling current. Due to the close proximity of the embedded sensing electrodes 1305 and the molecules under test, signal-to-noise ratio can be improved.

Figure 13B:
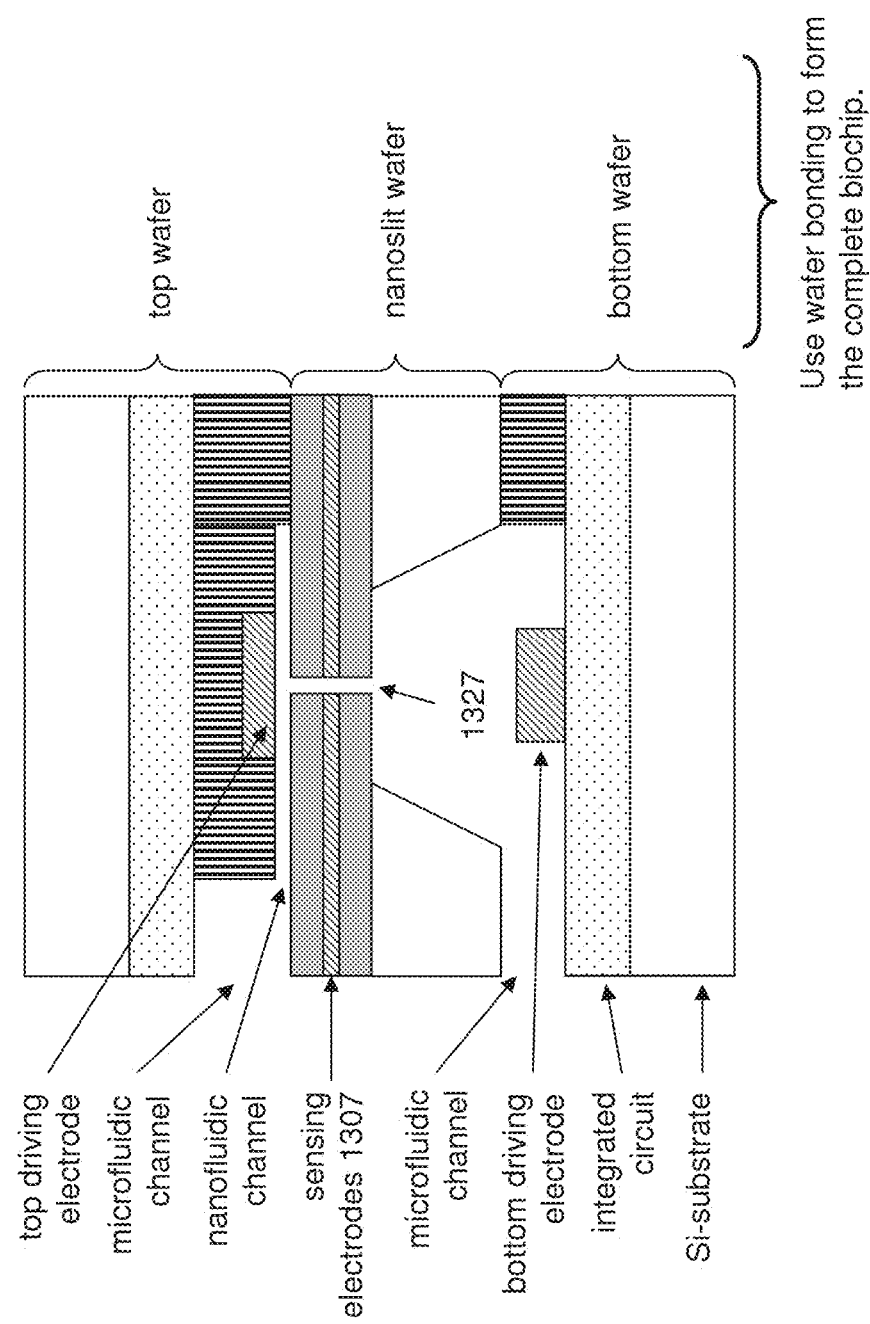
FIG. 13B illustrates one embodiment of a planar electrode implementation.
Figure 13C:
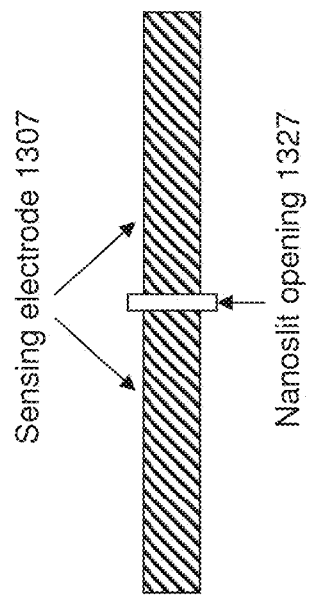
FIG. 13C illustrates a top view of one embodiment of sensing electrodes and nanoslit in planar electrode implementation.

The above exemplary sample delivery and filtering mechanism serves as an example to illustrate how an array of nanopore measurement chambers can be implemented. One of skill in the art would recognize that variations to the above delivery and filtering mechanism may be adopted in different embodiments. Furthermore, array of pores with different sizes can be realized using the illustrated methods. Together with the protein pores, such as α-haemolysin, and the above mentioned array of solid-state nanopores, an array of bio-nanopores can also be realized. In some embodiments, both sensing electrodes may be placed onto the same conducting layer, instead of the stacked electrodes on different conducting layers described above. FIG. 13B illustrates one embodiment of this planar electrode implementation. In this planar electrode implementation, both sensing electrodes 1307 are placed on the same conducting layer, with a nanoslit 1327 defined in between the sensing electrodes 1307. A top view of the sensing electrodes 1307 and the nanoslit 1327 are illustrated in FIG. 13C. As discussed above, both nanopore and nanoslit can be defined using the nanopantography.

The ability to perform molecule detection substantially in real-time, the ability to perform single molecule detection without the pre-detection sample amplification, the ability to carry out multiple and substantially simultaneous detections, the ability to do multi-pass detection, the ability to identify the sample without the computation intensive post-detection analysis, and/or the ability to retain the sample after detection for future use are very crucial in providing a low cost, fast and accurate genomic analysis in some embodiments, for instance, in recognizing the single nucleotide polymorphism.

Nanopore-Based Sequencer

Nanopore-based sequencer provides a portable genomic detection and analysis system. In some embodiments, the nanopore-based sequencer includes two major components, namely hardware and software. Some embodiments of the high level architectures and subunits are discussed below.

A. Hardware System

Figure 14:
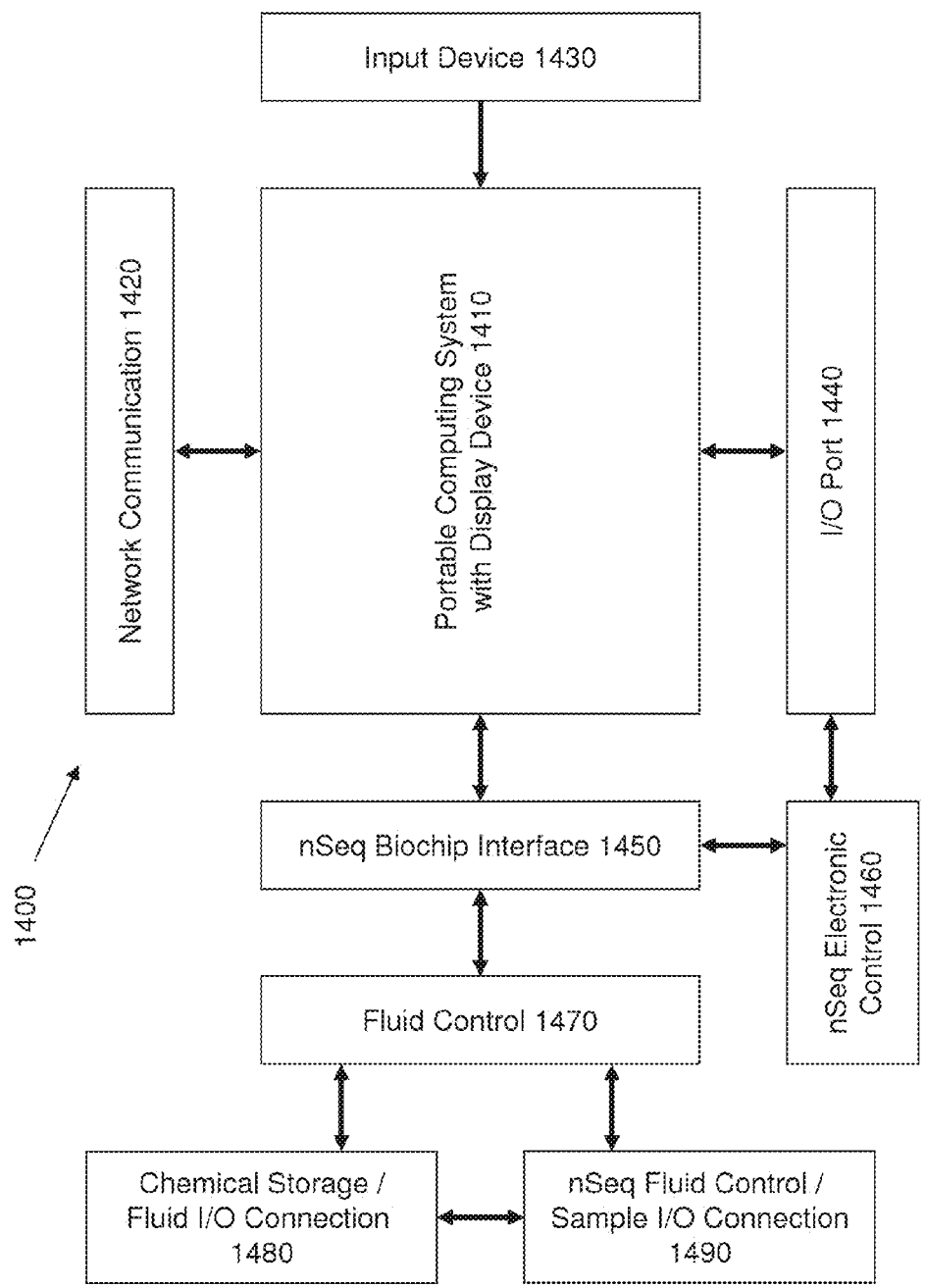
FIG. 14 illustrates a high-level hardware architecture of one embodiment of a nanopore-based sequencer.

In some embodiments, the hardware system of nanopore-based sequencer includes two major units, namely the computing, communication and control unit and the nanopore-based sequencing biochip interface unit, and various modules. One embodiment of the high level architecture is shown in FIG. 14. The details of various parts are further explained below.

I. Computing, Communication, and Control Unit

In one embodiment, the hardware system 1400 includes a portable computing system with a display device 1410. This may be implemented using a tablet, a laptop, a netbook, an all-in-one desktop computer, a smartphone, a personal digital assistant (PDA) or any handheld computing devices, etc. It serves as the central unit for running the operating system (OS), executing the data analysis software, storing data, controlling the operation of the nanopore-based sequencing biochip, and collecting data from the nanopore-based sequencing biochip.

In one embodiment, the hardware system 1400 further includes a network communication module 1420. The network communication module 1420 includes one or more of WiFi, WiMAX, Ethernet, Bluetooth, telephone capability, satellite link, and Global Positioning System (GPS), etc. The network communication module 1420 serves as the communication hub for communicating with the central computing system for data sharing, program update, data analysis, etc., communicating with other computing devices such that the data can be shared and the data analysis can be run in parallel in multiple computing devices, communicating with other bluetooth enabled devices (e.g., cellular telephone, printer, etc.), data sharing, program update, etc., and sending and receiving the GPS signal.

In one embodiment, the hardware system 1400 further includes an input device 1430. The input device 1430 may include one or more of a keyboard, a touch screen, a mouse, a trackball, infrared (IR) pointing device, and voice recognition device, etc. The input device 1430 serves as the human interface for command entry and data entry.

In one embodiment, the hardware system 1400 further includes an input/output (I/O) port 1440, which may include a flash memory card interface, an IEEE 1394 interface, and a Universal Serial Bus (USB) interface, etc. The I/O port 1440 serves as a serial interface with other electronic devices, a secondary data storage interface, and measurement data I/O for the nanopore-based sequencing biochip.

II. Nanopore-Based Sequencing Biochip Interface Unit

In some embodiments, a nanopore-based sequencing (nSeq) biochip interface unit 1450 couples to an nSeq electronic module 1460, a fluid control module 1470, a chemical storage and fluid I/O connection module 1480, and an nSeq fluid control and sample I/O connection module 1490. The nSeq electronic module 1460 controls the distribution of nucleic acid module, control the flow rate of the nanofluidic channels, collect measurement data, and output data to the computing, communication, and control unit.

In some embodiments, the fluid control module 1470 controls the fluid flow between the chemical storage and the nSeq biochip via the buffer intake/outlet connectors and the use of the on-chip or off-chip micropumps and microvalves. The chemical storage and fluid I/O connection module 1480 can supply chemical to the nSeq biochip, if needed, and can also serve as a chemical and/or bio-waste storage. The nSeq fluid control and sample I/O connection module 1490 can control the fluid and sample flow in the nSeq biochip as well as control the sample intake and outlet of the nSeq biochip. For instance, referring back to FIG. 10B, if one wants to perform detection at measurement chamber #11, the buffer outlet for branch #1 will be opened while all of the other buffer outlets are closed. As a result, the fluid will flow from the sample intake toward branch #1 and works in synchronous with the sample guiding electrodes along the microfluidic channels to deliver the sample to measurement chamber #11.

B. Software Architecture

Figure 15:
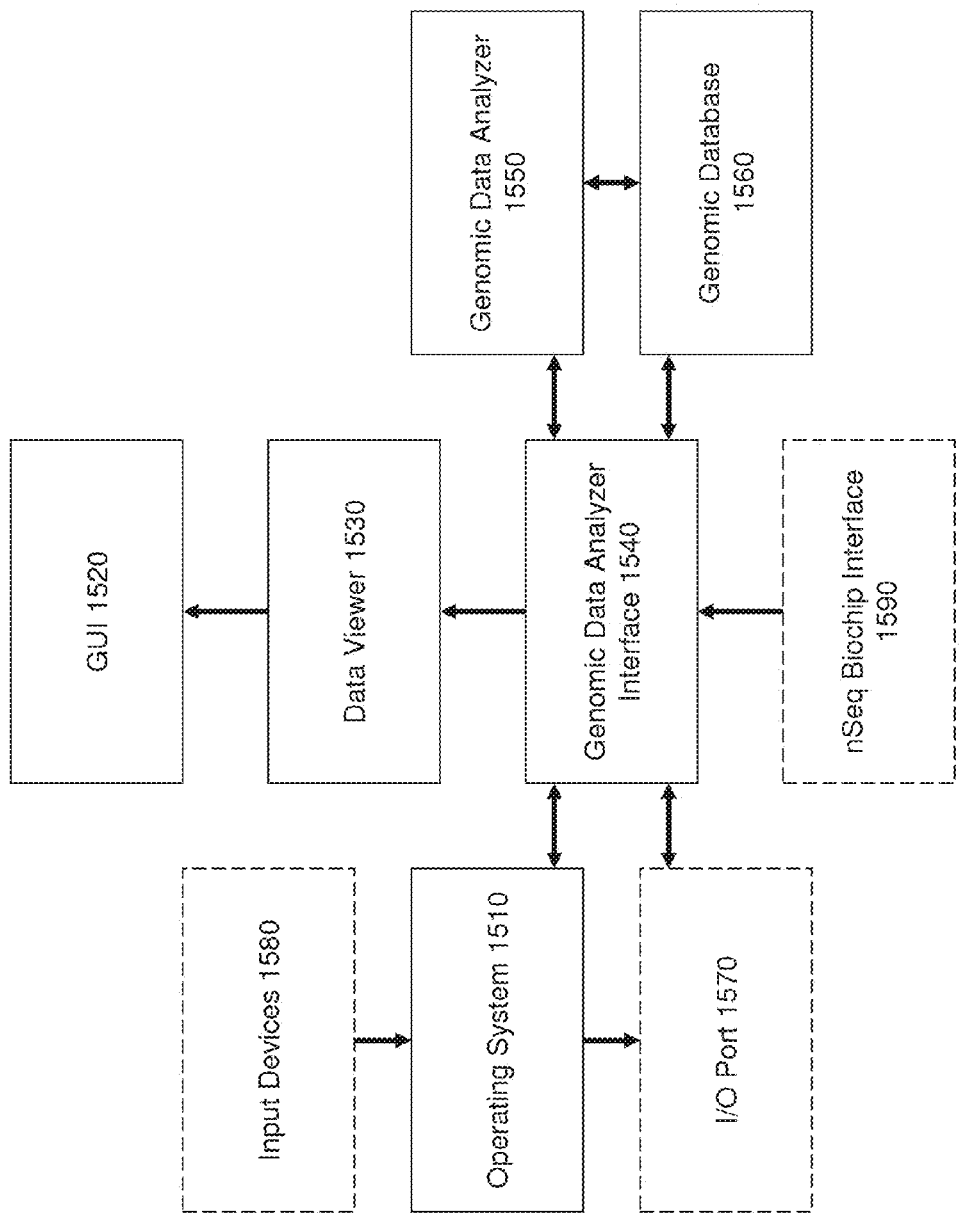
FIG. 15 illustrates a high-level architecture of the software and related hardware components for the operating system and the genomic analysis software in one embodiment of a nanopore-based sequencer.

FIG. 15 illustrates a high-level architecture of the software and related hardware components for the operating system and the genomic analysis software in one embodiment of a nanopore-based sequencer. Various logic processing modules in the software architecture shown can be implemented by processing devices (such as the portable computing system 1410 in FIG. 14) executing instructions embodied in computer-readable medium. A computer-readable medium includes any mechanism that provides (i.e., stores and/or transmits) information in a form accessible by a computer (e.g., a server, a personal computer, network device, personal digital assistant, manufacturing tool, any device with a set of one or more processors, etc.). For example, a computer-readable medium includes recordable/non-recordable media (e.g., read only memory (ROM); random access memory (RAM); magnetic disk storage media; optical storage media; flash memory devices; etc.); etc.

As mentioned above, an operating system 1510 is installed in the computing, communication and control unit. The operating system 1510 may include Windows, Linux, or any operating system suitable for computing devices. Aside from the operating system 1510 installed in the computing, communication and control unit, the genomic analysis software further includes five processing modules, namely, a graphical user interface (GUI) 1520, a data viewer 1530, a genomic data analyzer interface 1540, a genomic data analyzer 1550, and a genomic database 1560. Some embodiments of the interaction between the operating system 1510, the above processing modules 1520-1560, and the other hardware components are discussed below with reference to FIG. 15.

In some embodiments, the genomic data analyzer interface 1540 acts as a data flow control unit in the genomic analysis software architecture. After obtaining the commands and/or input data from the input device, the operating system 1510 transmits the information to the genomic data analyzer 1550 through the genomic data analyzer interface 1540. The genomic data analyzer 1550 then acts accordingly. With the proper commands (e.g., GET, ADD, etc.), the genomic data analyzer interface 1540 controls the data flow between the I/O port 1570 and the genomic database 1560, so the data stored in the database 1560 can be sent out or updated. Similarly, the analyzer software can be periodically updated via the I/O port 1570 and/or the input devices 1580. The genomic data analyzer interface 1540 is also coupled to the nSeq biochip interface 1590 to monitor the nSeq biochip. The status of the nSeq biochip is monitored and shown in a display unit (such as the display device in the portable computing system 1410 in FIG. 14) via the analyzer interface 1540. The genomic data analyzer interface 1540 also takes the results from the genomic data analyzer 1550 and shows them in the display unit.

In some embodiments, the genomic data analyzer 1550 is the main data analysis unit of the genomic analysis software. It obtains the measurements from the nSeq biochip, performs analysis and then compares the results with the data stored in the database 1560 to identify the bio-agents. The analysis results can be shown in the display unit and stored in the database 1560 for future reference.

The genomic database 1560 is a data repository for storing the existing bio-agents and newly discovered nucleic acid sequences. The data viewer 1530 includes software routines that take the data and information from some or all of the other units and show them on the display device.

Thus, a method and apparatus for portable real-time analysis and identification of molecules has been described. It will be apparent from the foregoing description that aspects of the present invention may be embodied, at least in part, in software. That is, the techniques may be carried out in a computer system or other data processing system in response to its processor executing sequences of instructions contained in a memory. In various embodiments, hardwired circuitry may be used in combination with software instructions to implement the present invention. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by a processor or controller.

It should be appreciated that references throughout this specification to "one embodiment" or "an embodiment" means that a particular feature, structure or characteristic described in connection with the embodiment is included in at least one embodiment of the present invention. Therefore, it is emphasized and should be appreciated that two or more references to "some embodiments" or "one embodiment" or "an alternative embodiment" in various portions of this specification are not necessarily all referring to the same embodiment. Furthermore, the particular features, structures or characteristics may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

I claim:

1. A nanopore-based sequencing chip, comprising:
   a first set of one or more sample guiding electrodes, which guide a sample toward a measurement chamber;
   a second set of one or more sample guiding electrodes, which guide the sample away from the measurement chamber;
   a nanopore array wafer comprising a plurality of nanopores;
   a top wafer bonded to a top side of the nanopore array wafer;
   a bottom wafer bonded to a bottom side of the nanopore array wafer,
   one or more nanofluidic channels defined by the top wafer and the nanopore array wafer;
   one or more microfluidic channels defined by the bottom wafer and the nanopore array wafer; and
   a plurality of measurement chambers,
   wherein each of the plurality of measurement chambers comprises a nanopore, a top driving electrode and a bottom driving electrode.

2. The nanopore-based sequencing chip of claim 1, wherein each of the plurality of nanopores is of a fixed identical size.

3. The nanopore-based sequencing chip of claim 1, further comprising:
   a first set of sensing and biasing circuits fabricated on the top wafer, wherein the top driving electrode in each of the plurality of measurement chambers is electrically coupled to the first set of sensing and biasing circuits; and
   a second set of sensing and biasing circuits fabricated on the bottom wafer, wherein the bottom driving electrode in each of the plurality of measurement chambers is electrically coupled to the second set of sensing and biasing circuits.

4. The nanopore-based sequencing chip of claim 1, wherein a second top driving electrodes and a second bottom driving electrode are embedded within each of said plurality of nanopores.

5. The nanopore-based sequencing chip of claim 1, further comprising:
   a plurality of sensing electrodes embedded within the nanopore array wafer, each of the plurality of sensing electrodes abutting one of the plurality of nanopores.

6. The nanopore-based sequencing chip of claim 5, wherein each of the plurality of sensing electrodes sense a signal selected from a group consisting of change in resistance, change in capacitance, change in phase and tunneling current.

7. The nanopore-based sequencing chip of claim 1, wherein each of the plurality of nanopores is a bio-nanopore.

8. The nanopore-based sequencing chip of claim 7, wherein the bio-nanopore is a protein pore.

9. The nanopore-based sequencing chip of claim 1, wherein the nanopore is a solid-state nanopore.

10. The nanopore-based sequencing chip of claim 1, wherein each of the plurality of measurement chambers performs independent analysis.

11. A nanopore-based sequencing chip, comprising:
    a nanopore array wafer, said nanopore array wafer comprising two layers of conductive materials sandwiching a layer of dielectric material and a plurality of nanopores that cuts across the thickness of the nanopore array wafer;
    a top wafer bonded to a top side of the nanopore array wafer;
    a bottom wafer bonded to a bottom side of the nanopore array wafer,
    one or more nanofluidic channels defined by the top wafer and the nanopore array wafer; and
    one or more microfluidic channels defined by the bottom wafer and the nanopore array wafer;
    wherein an AC sensing current is applied across said two layers of conductive materials to interrogate molecules translocating through said plurality of nanopores.

12. The nanopore-based sequencing chip of claim 11, wherein each of the plurality of nanopores is of a fixed identical size.

13. The nanopore-based sequencing chip of claim 11, further comprising:
- a top driving electrode coupled to a bottom side of the top wafer; and
- a bottom driving electrode coupled to a top side of the bottom wafer;
- wherein the top driving electrode is electrically coupled to a first set of sensing and biasing circuits, and the bottom driving electrode is electrically coupled to a second set of sensing and biasing circuits.

14. The nanopore-based sequencing chip of claim 11, wherein said nanopore array wafer further comprises a pair of driving electrodes.

* * * * *